United States Patent
Wu et al.

(10) Patent No.: US 12,288,599 B2
(45) Date of Patent: Apr. 29, 2025

(54) PROTEIN STRUCTURE INFORMATION PREDICTION METHOD AND APPARATUS, DEVICE, AND STORAGE MEDIUM

(71) Applicant: Tencent Technology (Shenzhen) Company Limited, Shenzhen (CN)

(72) Inventors: Jiaxiang Wu, Shenzhen (CN); Yuzhi Guo, Shenzhen (CN); Junzhou Huang, Shenzhen (CN)

(73) Assignee: TENCENT TECHNOLOGY (SHENZHEN) COMPANY LIMITED, Shenzhen (CN)

( * ) Notice: Subject to any disclaimer, the term of this patent is extended or adjusted under 35 U.S.C. 154(b) by 708 days.

(21) Appl. No.: 17/539,946

(22) Filed: Dec. 1, 2021

(65) Prior Publication Data
US 2022/0093213 A1 Mar. 24, 2022

Related U.S. Application Data

(63) Continuation of application No. PCT/CN2020/114386, filed on Sep. 10, 2020.

(30) Foreign Application Priority Data

Oct. 30, 2019 (CN) .......................... 201911042649.9

(51) Int. Cl.
*G01N 33/48* (2006.01)
*G01N 33/50* (2006.01)
(Continued)

(52) U.S. Cl.
CPC .............. *G16B 30/10* (2019.02); *G16B 5/00* (2019.02); *G16B 20/30* (2019.02); *G16B 50/00* (2019.02)

(58) Field of Classification Search
CPC .......... G16B 30/10; G16B 5/00; G16B 20/30; G16B 50/00
See application file for complete search history.

(56) References Cited

U.S. PATENT DOCUMENTS 7,157,266 B2 1/2007 Freimuth
2010/0057419 A1 3/2010 Nagarajaram et al.

FOREIGN PATENT DOCUMENTS

AU 2002250066 A1 8/2002
CN 104615911 A 5/2015
(Continued)

OTHER PUBLICATIONS

English machine translation of CN 105574359 A. (Year: 2024).*
(Continued)

*Primary Examiner* — Russell S Negin
(74) *Attorney, Agent, or Firm* — Crowell & Moring LLP

(57) ABSTRACT

This application provides a protein structure information prediction method and apparatus, a device, and a storage medium, and relates to the field of biological information technologies. The method includes: performing sequence alignment query in a first database according to an amino acid sequence of a protein to obtain multi-sequence aligned data; performing feature extraction on the multi-sequence aligned data to obtain an initial sequence feature; processing the initial sequence feature by using a sequence feature augmentation model to obtain an augmented sequence feature of the protein; and predicting structure information of the protein according to the augmented sequence feature. When the structure information of the protein is predicted based on artificial intelligence (AI), the foregoing solution can improve the prediction efficiency of protein structure information while ensuring the prediction accuracy of the protein structure information.

16 Claims, 7 Drawing Sheets

(51) Int. Cl.
  *G16B 5/00* (2019.01)
  *G16B 20/30* (2019.01)
  *G16B 30/10* (2019.01)
  *G16B 50/00* (2019.01)

(56) References Cited

FOREIGN PATENT DOCUMENTS

| | | |
|---|---|---|
| CN | 105574359 A | 5/2016 |
| CN | 106951736 A | 7/2017 |
| CN | 107563150 A | 1/2018 |
| CN | 108197427 A | 6/2018 |
| CN | 109255339 A | 1/2019 |
| CN | 109300501 A | 2/2019 |
| CN | 109411018 A | 3/2019 |
| CN | 110097130 A | 8/2019 |
| CN | 110706738 A | 1/2020 |
| WO | WO-2021026037 A1 * | 2/2021 ............... G06N 3/02 |

OTHER PUBLICATIONS

Mittal et al. Chapter 2: Modified single pass clustering algorithm based on median as a threshold similarity value. pp. 24-25. (Year: 2017).*

Office Action with English Translation of Concise Explanation of Relevance for Chinese Patent Application No. 201911042649.9 dated Aug. 28, 2020, 9 pages.

International Search Report and Written Opinion with English Translation for International Patent Application No. PCT/CN2020/114386 dated Dec. 8, 2020, 14 pages.

David R. Kelley, et al., "Gene prediction with Glimmer for metagenomic sequences augmented by classification and clustering", Published online Nov. 18, 2011, Nucleic Acid Research, 2012, vol. 40, No. 1 e9, pp. 1-12.

Fusong Ju, et al., "Seq-SetNet: Exploring Sequence Sets for Inferring Structures", arXiv:1906.11196v1 [q-bio-BM] Jun. 6, 2019, pp. 1-9.

Xiaoqing Yu, Collection of China Ph.D. Theses; Database Fundamental Science Series, "The Study of Biological Data Analysis Method Based on Support Vector Machines", Dec. 15, 2012, 77 pages.

Japanese Decision to Grant a Patent issued May 10, 2023 in corresponding Japanese Patent Application No. 2022-514493 with English translation, 5 pages.

Examination Report for European Patent Application No. 20882879.8 dated Jul. 14, 2023, 6 pages.

Extended European Search Report for European Patent Application No. 20882879.8 dated Aug. 11, 2022, 10 pages.

Ma, Yuming et al: "Protein Secondary Structure Prediction Based on Data Partition and Semi-Random Subspace Method", Scientific Reports, vol. 8, No. 1, Jun. 29, 2018 (Jun. 29, 2018), XP55947635, DOI: 10.1038/s41598-018-28084-8.

Atasever, Sema et al: "Sample Reduction Strategies for Protein Secondary Structure Prediction", Applied Sciences, vol. 9, No. 20, Oct. 18, 2019 (Oct. 18, 2019), XP55947943, ISSN: 2076-3417, DOI: 10.3390/app9204429.

* cited by examiner

PROTEIN STRUCTURE INFORMATION PREDICTION METHOD AND APPARATUS, DEVICE, AND STORAGE MEDIUM

RELATED APPLICATION

This application is a continuation application of the International PCT Application No. PCT/CN2020/114386, filed with the China National Intellectual Property Administration, PRC on Sep. 10, 2020 which claims priority to Chinese Patent Application No. 201911042649.9, filed with the China National Intellectual Property Administration, PRC on Oct. 30, 2019, each of which is incorporated herein by reference in their entireties.

FIELD OF THE TECHNOLOGY

This application relates to the field of biological information technologies, and in particular, to a protein structure information prediction method and apparatus, a device, and a storage medium.

BACKGROUND OF THE DISCLOSURE

The actual role of a protein in an organism is closely related to its three-dimensional structure. Therefore, it is of great significance to accurately determine the three-dimensional structure of a protein.

Since the three-dimensional structure of a protein is essentially determined by its corresponding amino acid sequence information, in the related art, the structure information of the protein can be determined by the amino acid sequence of the protein. For example, when structure information of a protein is determined by an amino acid sequence of the protein, a multi-sequence aligned data query operation is first performed in an amino acid sequence database according to the amino acid sequence of the protein to extract sequence features of the amino acid sequence of the protein, and the structure information of the protein is then predicted according to the sequence features. The accuracy of the foregoing sequence feature extraction is directly related to the data scale of the database. The larger the data scale of the amino acid sequence database is, the higher the accuracy of the sequence feature extraction is.

However, in the related art, to extract more accurate sequence features, it is necessary to perform a query operation based on a database with a larger data scale, but the database with a larger data scale causes the query operation to take a long time, leading to a lower prediction efficiency of protein structure information.

SUMMARY

Embodiments of this disclosure provide a protein structure information prediction method and apparatus, a device, and a storage medium, which can improve the prediction efficiency of protein structure information while ensuring the prediction accuracy of the protein structure information. The technical solution is as follows:

According to an aspect, a protein structure information prediction method is provided, including:

performing sequence alignment query in a first database according to an amino acid sequence of a protein to obtain multi-sequence aligned data;

performing feature extraction on the multi-sequence aligned data to obtain an initial sequence feature;

processing the initial sequence feature by using a sequence feature augmentation model to obtain an augmented sequence feature of the protein, the sequence feature augmentation model being a machine learning model trained by using an initial sequence feature sample and an augmented sequence feature sample, the initial sequence feature sample being obtained by performing sequence alignment query in the first database according to an amino acid sequence sample, the augmented sequence feature sample being obtained by performing sequence alignment query in a second database according to the amino acid sequence sample, and a data scale of the second database being greater than a data scale of the first database; and predicting structure information of the protein based on the augmented sequence feature.

According to an aspect, a protein structure information prediction apparatus is provided, including:

a data obtaining module, configured to perform sequence alignment query in a first database according to an amino acid sequence of a protein to obtain multi-sequence aligned data;

an initial feature obtaining module, configured to perform feature extraction on the multi-sequence aligned data to obtain an initial sequence feature;

an augmented feature obtaining module, configured to process the initial sequence feature by using a sequence feature augmentation model to obtain an augmented sequence feature of the protein, the sequence feature augmentation model being a machine learning model trained by using an initial sequence feature sample and an augmented sequence feature sample, the initial sequence feature sample being obtained by performing sequence alignment query in the first database according to an amino acid sequence sample, the augmented sequence feature sample being obtained by performing sequence alignment query in a second database according to the amino acid sequence sample, and a data scale of the second database being greater than a data scale of the first database; and a structure information prediction module, configured to predict structure information of the protein based on the augmented sequence feature.

In one implementation, a data distribution similarity between the first database and the second database is higher than a similarity threshold.

In one implementation, the first database is a database obtained by randomly removing a specified proportion of data based on the second database.

In one implementation, the sequence feature augmentation model is a fully convolutional network (FCN) model for one-dimensional sequence data, or a recurrent neural network (RNN) model including a plurality of layers of long short-term memory (LSTM) units or an RNN model including bidirectional LSTM units.

In one implementation, the initial sequence feature and the augmented sequence feature are position-specific scoring matrices (PSSMs).

In one implementation, the apparatus further includes:

an augmented sample obtaining module, configured to process the initial sequence feature sample by using the sequence feature augmentation model to obtain an augmented initial sequence feature sample; and a model update module, configured to update the sequence feature augmentation model according to the augmented initial sequence feature sample and the augmented sequence feature sample.

In one implementation, the model update module includes:

a loss function obtaining submodule, configured to perform a loss function calculation according to the augmented initial sequence feature sample and the augmented sequence feature sample to obtain a loss function value; and a parameter update submodule, configured to update a model parameter in the sequence feature augmentation model according to the loss function value.

In one implementation, the loss function obtaining submodule includes:

an error calculation unit, configured to calculate a reconstruction error between the augmented initial sequence feature sample and the augmented sequence feature sample; and a loss function acquisition unit, configured to acquire the reconstruction error as the loss function value.

In one implementation, the error calculation unit calculates a root mean square reconstruction error between the augmented initial sequence feature sample and the augmented sequence feature sample.

In one implementation, the model update module is configured to, in a case that the sequence feature augmentation model is determined not to converge according to the loss function value, update the model parameter in the sequence feature augmentation model according to the loss function value.

In one implementation, the structure information prediction module includes:

a structure information obtaining submodule, configured to predict the augmented sequence feature by using a protein structure information prediction model to obtain the structure information of the protein, where the protein structure information prediction model is a model trained according to a sequence feature of a protein sample and structure information of the protein sample.

According to an aspect, a computer device is provided, including a processor and a memory, the memory storing at least one instruction, at least one program, a code set, or an instruction set, the at least one instruction, the at least one program, the code set, or the instruction set being loaded and executed by the processor to implement the foregoing protein structure information prediction method.

According to an aspect, a non-transitory computer-readable storage medium is provided, storing at least one instruction, at least one program, a code set, or an instruction set, the at least one instruction, the at least one program, the code set, or the instruction set being loaded and executed by a processor to implement the foregoing protein structure information prediction method.

According to an aspect of this application, a computer program product or a computer program is provided, including computer instructions, the computer instructions being stored in a non-transitory computer-readable storage medium. A processor of a computer device reads a computer instruction from a computer-readable storage medium, and executes the computer instruction, so that the computer device performs the protein structure information prediction method provided in various optional implementations of the foregoing aspects.

The technical solution provided in this application may include the following beneficial effects:

In the solution shown in the embodiments of this disclosure, by performing sequence alignment query on an amino acid sequence of a protein and performing feature extraction on multi-sequence aligned data, an augmented sequence feature of the protein is obtained by using a sequence feature augmentation model, and then structure information of the protein is predicted. By using the sequence feature augmentation model, the sequence alignment query only needs to be performed in a first database with a smaller data scale to obtain higher prediction accuracy. In addition, it takes less time to perform the sequence alignment query in the first database with a smaller data scale. Therefore, the foregoing solution can improve the prediction efficiency of protein structure information while ensuring the prediction accuracy of the protein structure information.

It is to be understood that, the foregoing general descriptions and the following detailed descriptions are merely for illustration and explanation purposes and are not intended to limit this application.

BRIEF DESCRIPTION OF THE DRAWINGS

Accompanying drawings herein are incorporated into a specification and constitute a part of this specification, show embodiments that conform to this application, and are used for describing a principle of this application together with this specification.

DESCRIPTION OF EMBODIMENTS

Figure 1:
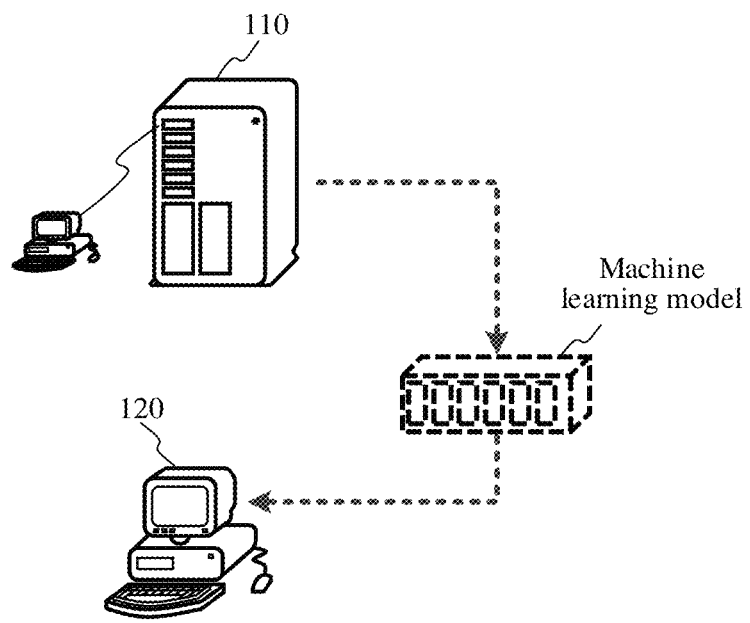
FIG. 1 is a framework diagram of model training and protein structure information prediction according to an exemplary embodiment of this disclosure.

Exemplary embodiments are described in detail herein, and examples of the exemplary embodiments are shown in the accompanying drawings. When the following description involves the accompanying drawings, unless otherwise indicated, the same numerals in different accompanying drawings represent the same or similar elements. The implementations described in the following exemplary embodiments do not represent all implementations that are consistent with this application. On the contrary, the implementations are merely examples of apparatuses and methods that are described in detail in the appended claims and that are consistent with some aspects of this application.

It is to be understood that, in this specification, "several" refers to one or more, and "plurality of" refers to two or more. "And/or" describes an association relationship between associated objects and represents that three relationships may exist. For example, A and/or B may represent the following three cases: only A exists, both A and B exist, and only B exists. The character "/" generally indicates an "or" relationship between the associated objects.

This application provides a protein structure information prediction method, which can recognize structure information of a protein through artificial intelligence (AI) to provide an efficient and high-accuracy protein structure information prediction solution. For ease of understanding, several terms involved in this application are explained below.

1) Amino Acid Sequence

Amino acids are compounds in which a hydrogen atom on a carbon atom of a carboxylic acid is substituted with an amino group. An amino acid molecule contains amino and carboxyl functional groups. Similar to hydroxy acids, amino acids can be classified according to different locations of an amino group attached to a carbon chain as $\alpha$-, $\beta$-, $\gamma$-, . . . , and w-amino acids, but the amino acids obtained after protein hydrolysis are only more than twenty $\alpha$-amino acids, which are the basic units that make up proteins. The 20 amino acids that make up human proteins are glycine, alanine, valine, leucine, isoleucine, phenylalanine, proline, tryptophan, serine, tyrosine, cysteine, methionine, asparagine, glutamine, threonine, aspartic acid, glutamic acid, lysine, arginine, and histidine. Compounds containing a plurality of peptide bonds formed by dehydration and condensation of these 20 amino acid molecules are polypeptides. A polypeptide is usually a chain structure, which is also referred to as a peptide chain. A peptide chain can be twisted and folded to form a protein molecule with a certain spatial structure.

2) Protein Structure

The protein structure refers to a spatial structure of a protein molecule. A protein is mainly composed of chemical elements of carbon, hydrogen, oxygen, nitrogen, and the like, which is an important biological macromolecule. All proteins are multimers formed by linking 20 different amino acids. The remaining of the amino acids after forming a protein is referred to as a residue.

The molecular structure of a protein can be classified into four levels to describe different aspects thereof:

A primary structure is a linear amino acid sequence that forms a polypeptide chain of the protein.

A secondary structure is a stable structure formed by hydrogen bonds between C=O and N—H groups between different amino acids, mainly an $\alpha$-helix and a $\beta$-sheet.

A tertiary structure is a three-dimensional structure of a protein molecule formed by arranging a plurality of secondary structure elements in a three-dimensional space.

A quaternary structure is used for describing functional protein compound molecules formed by the interaction between different polypeptide chains (subunits).

3) Artificial Intelligence (AI)

AI involves a theory, a method, a technology, and an application system that use a digital computer or a machine controlled by the digital computer to simulate, extend, and expand human intelligence, perceive an environment, obtain knowledge, and use knowledge to obtain an optimal result. In other words, AI is a comprehensive technology of computer science, which attempts to understand essence of intelligence and produces a new intelligent machine that can react in a manner similar to human intelligence. AI is to study the design principles and implementation methods of various intelligent machines, to enable the machines to have the functions of perception, reasoning, and decision-making.

The AI technology is a comprehensive discipline and relates to a wide range of fields including both hardware-level technologies and software-level technologies. The basic AI technologies generally include technologies such as a sensor, a dedicated AI chip, cloud computing, distributed storage, a big data processing technology, an operating/interaction system, and electromechanical integration. AI software technologies mainly include several major directions such as a computer vision (CV) technology, a speech processing technology, a natural language processing technology, and machine learning (ML)/deep learning.

4) Machine Learning (ML)

ML is a multi-disciplinary subject involving a plurality of disciplines such as probability theory, statistics, approximation theory, convex analysis, and algorithm complexity theory. ML specializes in studying how a computer simulates or implements a human learning behavior to obtain new knowledge or skills, and reorganize an existing knowledge structure, so as to keep improving its performance. ML is the core of AI, is a basic way to make the computer intelligent, and is applied to various fields of AI. ML and deep learning generally include technologies such as an artificial neural network, a belief network, reinforcement learning, transfer learning, inductive learning, and learning from demonstrations.

The solution of the embodiments of this disclosure includes a model training stage and a prediction stage. FIG. 1 is a framework diagram of model training and protein structure information prediction according to an exemplary embodiment. As shown in FIG. 1, in the model training stage, a model training device 110 trains a machine learning model by performing a multi-sequence aligned data query operation and a sequence feature extraction operation on amino acid sequences corresponding to the same protein in databases with different scales; and in the prediction stage, a prediction device 120 may predict structure information of the protein corresponding to the amino acid sequences according to the trained machine learning model and the inputted amino acid sequences.

The model training device 110 and the prediction device 120 may be computer devices with a machine learning capability. For example, the computer device may be a fixed computer device such as a personal computer, a server, or a fixed research device; alternatively, the computer device may be a mobile computer device such as a tablet computer, or an e-book reader.

In one implementation, the model training device 110 and the prediction device 120 may be the same device or may be different devices. When the model training device 110 and the prediction device 120 are different devices, the model training device 110 and the prediction device 120 may be devices of the same type, for example, the model training device 110 and the prediction device 120 both may be personal computers; alternatively, the model training device 110 and the prediction device 120 may be devices of different types, for example, the model training device 110 may be a server, and the prediction device 120 may be a fixed research experimental device, or the like. A specific type of the model training device 110 and the prediction device 120 is not limited in the embodiments of this disclosure.

Figure 2:
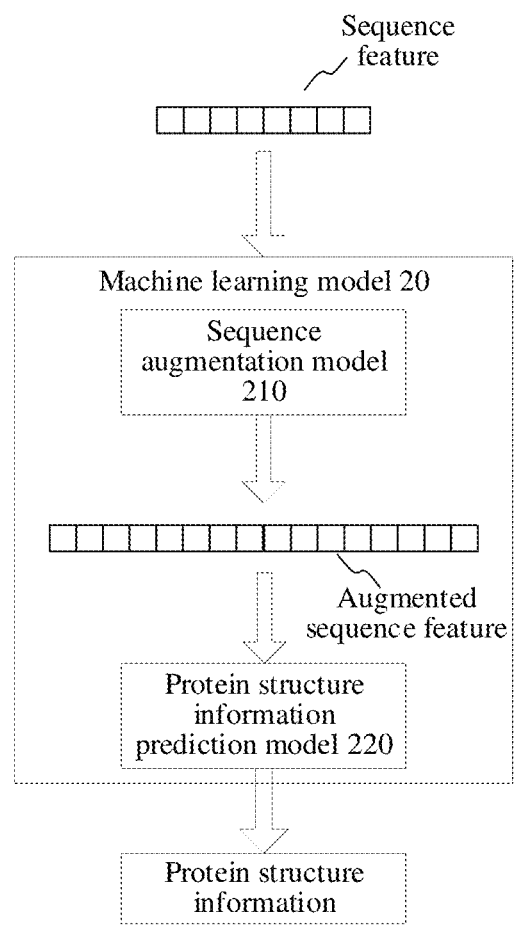
FIG. 2 is a model architecture diagram of a machine learning model according to an exemplary embodiment of this disclosure.

FIG. 2 is a model architecture diagram of a machine learning model according to an exemplary embodiment. As shown in FIG. 2, a machine learning model 20 in this embodiment of this disclosure may include two models, where a sequence feature augmentation model 210 is used for automatically augmenting an inputted sequence feature and outputting an augmented sequence feature. In addition to outputting the augmented sequence feature, the sequence feature augmentation model 210 may further input the augmented sequence feature into a protein structure information prediction model 220. The protein structure information prediction model 220 is used for predicting protein structure information according to the augmented sequence feature inputted by the sequence feature augmentation model 210 and outputting a prediction result of the protein structure information.

In the machine learning model shown in FIG. 2, the protein structure information prediction does not only use the feature sequence extracted from a single database through the multi-sequence aligned data query as data inputted into the protein structure information prediction model, but also uses the augmented sequence feature as the inputted data for predicting the protein structure information. Compared with the sequence feature obtained from the single database through comparison, the automatically augmented sequence feature is more accurate in predicting the protein structure information.

Proteins have important practical roles in organisms. For example, proteins can cause some genetic diseases, or proteins can make organisms immune to specific diseases. The role of a protein in an organism is largely determined by a three-dimensional structure of the protein. The three-dimensional structure of the protein is essentially determined by amino acid sequence information corresponding to the protein.

The three-dimensional structure of the protein may be determined by experimental methods. For example, the three-dimensional structure of the protein may be determined by methods such as X-ray crystallography, nuclear magnetic resonance, and cryogenic electron microscopy. Due to the high time and economic costs of determining the three-dimensional structure of the protein based on the experimental methods, it is of high scientific significance and practical value to directly predict the three-dimensional structure of the protein according to the amino acid sequence corresponding to the protein by calculation methods rather than the experimental methods.

In the process of predicting the three-dimensional structure of the protein based on the calculation methods, whether part of the structure information of the protein can be accurately predicted ultimately determines the prediction accuracy of the three-dimensional structure of the protein to a large extent. The part of the structure information of the protein includes a backbone dihedral angle, a secondary structure, or the like. Therefore, in view of the conflict between prediction accuracy and calculation efficiency in a protein structure information prediction algorithm based on a sequence feature, the protein structure information prediction method provided in this application can reduce a data scale requirement of an amino acid sequence database, obtain the prediction accuracy of the protein structure information similar to that obtained by a conventional method with lower database storage and query costs, and improve the prediction accuracy and calculation efficiency of the protein structure information, thereby promoting the improvement of the prediction accuracy of the three-dimensional structure of the protein.

Figure 3:
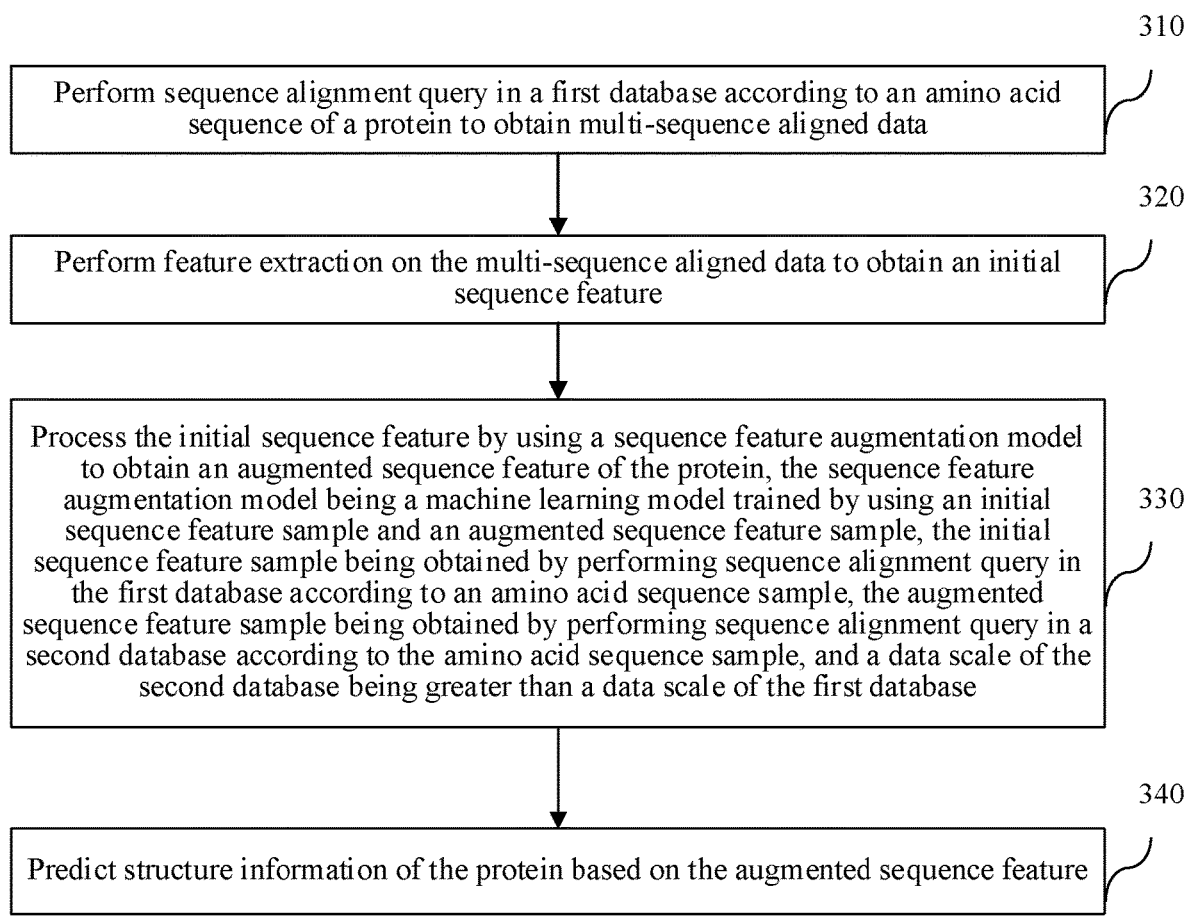
FIG. 3 is a schematic flowchart of a protein structure information prediction method according to an exemplary embodiment of this disclosure.

FIG. 3 is a schematic flowchart of a protein structure information prediction method according to an exemplary embodiment of this disclosure. The protein structure information prediction method may be performed by a computer device, for example, the prediction device 120 shown in FIG. 1. As shown in FIG. 3, the protein structure information prediction method may include the following steps:

Step 310. Perform sequence alignment query in a first database according to an amino acid sequence of a protein to obtain multi-sequence aligned data.

In this embodiment of this disclosure, the computer device may obtain the multi-sequence aligned data through a sequence alignment operation.

The sequence alignment refers to aligning a plurality of amino acid sequences and highlighting similar structure regions therein. By comparing an amino acid sequence corresponding to a known protein structure and function with an amino acid sequence corresponding to an unknown protein structure and function, homology between the two amino acid sequences is determined, so as to predict the protein structure and function composed of unknown amino acid sequences.

In one implementation, the first database is a database including several amino acid sequences.

Step 320. Perform feature extraction on the multi-sequence aligned data to obtain an initial sequence feature.

In this embodiment of this disclosure, the prediction device may obtain a homologous sequence in the first database through the multi-sequence aligned data query operation by using a position-specific iterative basic local alignment search tool (PSI-BLAST) for each amino acid sequence, and then obtain a position-specific scoring matrix (PSSM) by comparing homology information of each sequence. The PSSM is the foregoing sequence feature.

The PSSM may be expressed as a frequency value of the amino acid appearing at a corresponding location obtained after the multi-sequence alignment is performed on the amino acid sequence, or a frequency of each amino acid appearing at each corresponding location, or a probability of each amino acid appearing at each corresponding location.

Step 330. Process the initial sequence feature by using a sequence feature augmentation model to obtain an augmented sequence feature of the protein.

In this embodiment of this disclosure, the prediction device may input the initial sequence feature into the sequence feature augmentation model, and the sequence feature augmentation model performs feature augmentation on the initial sequence feature, that is, adds a new feature to the initial sequence feature to obtain a more comprehensive augmented sequence feature.

The sequence feature augmentation model is a machine learning model trained by using an initial sequence feature sample and an augmented sequence feature sample, the initial sequence feature sample is obtained by performing sequence alignment query in the first database according to an amino acid sequence sample, the augmented sequence feature sample is obtained by performing sequence alignment query in a second database according to the amino acid sequence sample, and a data scale of the second database is greater than a data scale of the first database. In some embodiments, the data scale may include the number of entries or records in a database.

In this embodiment of this disclosure, in the training process of the sequence feature augmentation model, the computer device may use the initial sequence feature sample as an input of the sequence feature augmentation model, and use the augmented sequence feature sample as labeled data of the initial sequence feature sample, to train the sequence feature augmentation model.

In this embodiment of this disclosure, the sequence feature augmentation model may be an FCN model for one-dimensional sequence data.

A convolutional neural network (CNN) is a feedforward neural network. Artificial neurons in the CNN may respond to surrounding units in a partial coverage area, and therefore there is excellent performance for large-scale image processing. The CNN includes a convolutional layer and a pooling layer. From CNN to FCN, the CNN is usually connected to several fully connected layers after the convolutional layer, and a feature map generated by the convolutional layer is mapped into a fixed-length feature vector.

In one implementation, the sequence feature augmentation model is an RNN model including a plurality of layers of LSTM units or an RNN model including bidirectional LSTM units.

The RNN is a type of recursive neural network in which sequence data is used as an input, recursion is performed in a sequence evolution direction, and all nodes, that is, recurrent units, are in a chain connection.

Step 340. Predict structure information of the protein based on the augmented sequence feature.

In this embodiment of this disclosure, the prediction device predicts the structure information of the protein, including, but not limited to, predicting a backbone dihedral angle of the protein and/or a secondary structure of the protein.

The dihedral angle is between two adjacent amide planes and can rotate with common Ca as a fixed point. An angle that rotates around a Ca—N bond is referred to as a φ angle, and an angle that rotates around a C—Ca bond is referred to as a ψ angle. The φ angle and the ψ angle are referred to as dihedral angles. In a protein, only the two bonds connected to an α-carbon atom, that is, the Ca—N bond and the C—Ca bond, are single bonds and can rotate freely. A backbone chain of a peptide chain may be composed of many planes separated by Ca. A dihedral angle determines relative locations of two peptide planes and then determines a location and a conformation of the backbone chain of the peptide chain.

The secondary structure of the protein refers to a specific conformation formed by the twisting or folding of polypeptide backbone atoms along a certain axis, that is, the spatial arrangement of the peptide backbone atoms does not involve side chains of amino acid residues. Main forms of the secondary structure of the protein include an α-helix, a β-sheet, a β-turn, and a random coil. Due to a large molecular mass of a protein, different peptide fragments of a protein molecule may contain secondary structures in different forms. In a protein, a main force for keeping a secondary structure is a hydrogen bond. The secondary structures of a protein are not just α-helix structures or β-sheet structures, but also include a combination of these different types of conformations. In different proteins, proportions of different types of conformations may also vary.

In summary, in the solution shown in the embodiments of this disclosure, by performing sequence alignment query on an amino acid sequence of a protein and performing feature extraction on multi-sequence aligned data, an augmented sequence feature of the protein is obtained by using a sequence feature augmentation model, and then structure information of the protein is predicted. By using the sequence feature augmentation model, the sequence alignment query only needs to be performed in a first database with a smaller data scale to obtain higher prediction accuracy. In addition, it takes less time to perform the sequence alignment query in the first database with a smaller data scale. Therefore, the foregoing solution can improve the prediction efficiency of protein structure information while ensuring the prediction accuracy of the protein structure information.

Figure 4:
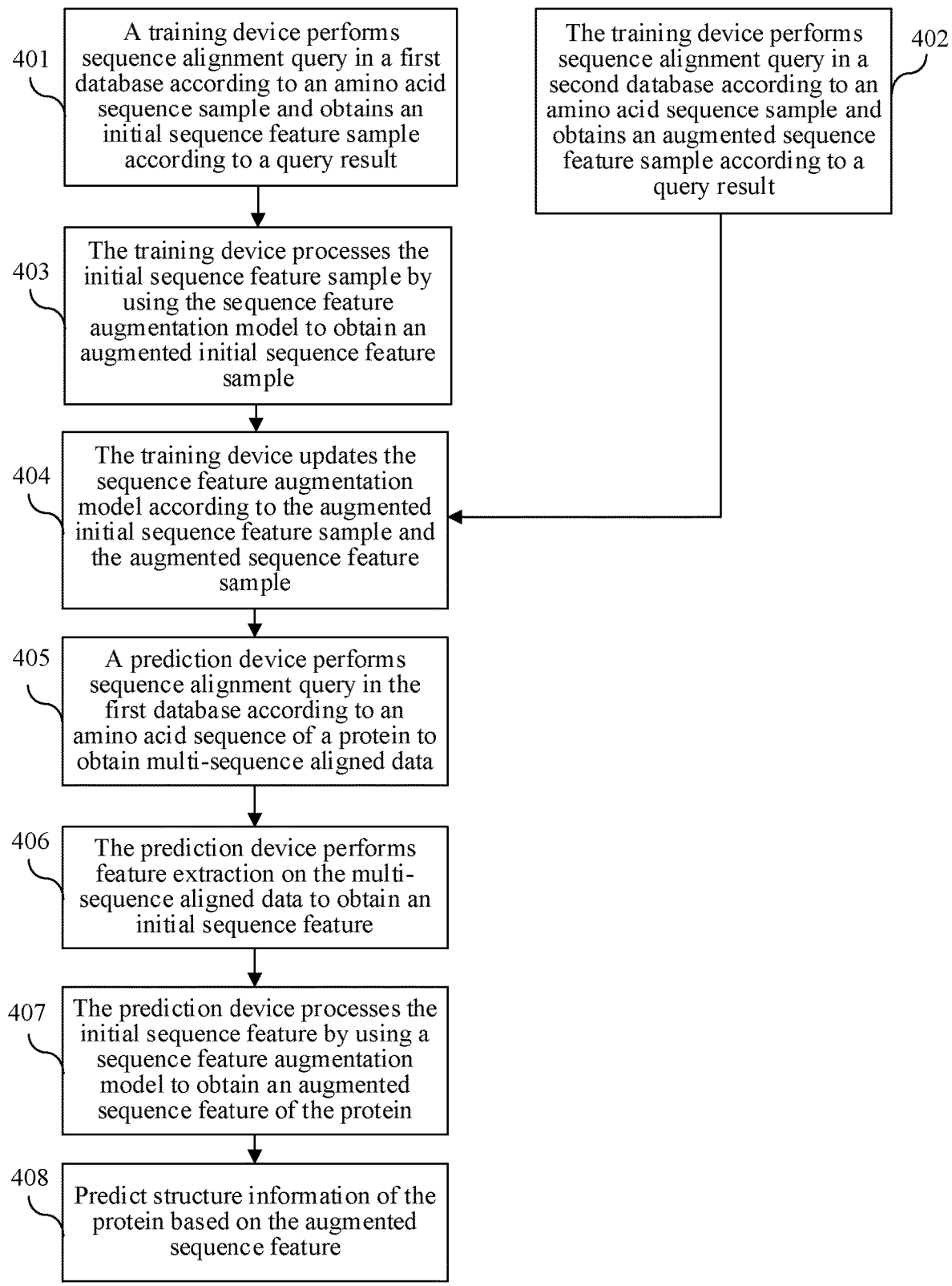
FIG. 4 is a schematic flowchart of a machine learning model training and protein structure information prediction method according to an exemplary embodiment of this disclosure.

FIG. 4 is a schematic flowchart of a machine learning model training and protein structure information prediction method according to an exemplary embodiment of this disclosure. The solution is divided into two parts: machine learning model training and protein structure information prediction. The machine learning model training and protein structure information prediction method may be performed by a computer device. The computer device may include the training device 110 and the prediction device 120 shown in FIG. 1. As shown in FIG. 4, the machine learning model training and protein structure information prediction method may include the following steps:

Step 401. A training device performs sequence alignment query in a first database according to an amino acid sequence sample and obtains an initial sequence feature sample according to a query result.

In this embodiment of this disclosure, the training device may perform the sequence alignment query in the first database according to the amino acid sequence sample to obtain multi-sequence aligned data, and then perform feature extraction on the multi-sequence aligned data to obtain the initial sequence feature sample.

In this embodiment of this disclosure, an amino acid sequence of a certain protein may be composed of a plurality of amino acids (for example, 20 known essential amino acids). The amino acid sequence sample may be a currently known amino acid sequence of a protein, or the amino acid sequence sample may be an amino acid sequence generated randomly or according to a certain rule.

In one implementation, the amino acid sequence sample includes an amino acid sequence with known protein structure information, or an amino acid sequence with unknown protein structure information, or both an amino acid sequence with known protein structure information and an amino acid sequence with unknown protein structure information.

Step 402. The training device performs sequence alignment query in a second database according to an amino acid sequence sample and obtains an augmented sequence feature sample according to a query result.

In this embodiment of this disclosure, the training device may perform the sequence alignment query in the second database according to the amino acid sequence sample to obtain multi-sequence aligned data, and then perform feature extraction on the multi-sequence aligned data to obtain the augmented sequence feature sample.

The training device obtains the initial sequence feature sample and the augmented sequence feature sample respectively from the first database and the second database through the same amino acid sequence sample, and the initial sequence feature sample and the augmented sequence feature sample are in one-to-one correspondence.

The initial sequence feature sample and the augmented sequence feature sample may be sequence features extracted according to the same feature extraction algorithm. For example, the initial sequence feature sample and the augmented sequence feature sample both may be PSSMs, and types of elements in the matrices are the same.

A data scale of the second database is greater than a data scale of the first database.

In this embodiment of this disclosure, the first database and the second database are amino acid sequence databases. Each database includes several amino acid sequences, and the quantity of amino acid sequences included in the second database is greater than the quantity of amino acid sequences included in the first database.

In one implementation, a data distribution similarity between the first database and the second database is higher than a similarity threshold.

In this embodiment of this disclosure, to improve the accuracy of subsequent sequence feature augmentation model training, the first database and the second database may use databases with similar data distributions, that is, the data distribution similarity between the first database and the second database needs to be higher than the predetermined similarity threshold.

The similarity threshold may be a value preset by a developer.

In one implementation, the first database and the second database are the same type of database, but have different data scales.

For example, the databases may be two existing databases with similar data distributions. For example, the first database and the second database may be UniRef databases with different data scales, or the first database and the second database may be a Swiss-Prot database and a TrEMBL database in a UniProtKB database.

The UniRef database may be divided into three levels 100%, 90%, and 50% according to identity, respectively UniRef100, UniRef90, and UniRef50 databases. Data volumes of these three databases UniRef100, UniRef90, and UniRef50 are reduced by 10%, 40%, and 70% respectively based on a complete database.

In one implementation, the first database may be the UniRef50 database, and the second database may be the UniRef90 or UniRef100 database (a data scale of the UniRef50 database is less than a data scale of the UniRef90 or UniRef100 database). Alternatively, the first database may be the UniRef90 database, and the second database may be the UniRef100 database.

In another implementation, the first database is a database obtained by removing a specified proportion of data based on the second database. For example, the removal of records in a database may follow a predetermined pattern or rule, and the pattern or rule maybe further be based on an index, or a keyword of the records. For another example, the removal of the records may be conducted in a random manner.

The specified proportion may be a proportion preset by a developer.

In this embodiment of this disclosure, the training device may randomly remove a specified proportion (for example, 50%) of amino acid sequences based on the second database to obtain the first database.

For example, the second database may be an existing database. For another example, the second database may be the UniRef90 database (or may be another existing database). The training device may randomly remove general amino acid sequences in the UniRef90 database to obtain the first database. The removal of the general amino acid sequences in the database may also follow a predetermined pattern or rule, and the pattern or rule maybe further be based on an index, or a keyword of the database.

Step 403. The training device processes the initial sequence feature sample by using the sequence feature augmentation model to obtain an augmented initial sequence feature sample.

In this embodiment of this disclosure, the computer device processes the initial sequence feature sample by using the sequence feature augmentation model to obtain the augmented initial sequence feature sample, which is similar to the process of obtaining the augmented sequence feature in the embodiment shown in FIG. 3. Details are not repeated herein.

Different from the embodiment shown in FIG. 3, the sequence feature augmentation model in this step may be a model that has not finished training.

Step 404. The training device updates the sequence feature augmentation model according to the augmented initial sequence feature sample and the augmented sequence feature sample.

In this embodiment of this disclosure, the training device performs a loss function calculation according to the augmented initial sequence feature sample and the augmented sequence feature sample to obtain a loss function value. Then, the training device updates a model parameter in the sequence feature augmentation model according to the loss function value.

In one implementation, the training device calculates a reconstruction error between the augmented initial sequence feature sample and the augmented sequence feature sample, and acquires the reconstruction error as the loss function value.

In one implementation, the reconstruction error is a root mean square reconstruction error. That is, when the reconstruction error is obtained, the training device calculates the root mean square reconstruction error between the augmented initial sequence feature sample and the augmented sequence feature sample, and acquires the root mean square reconstruction error as the loss function value.

For example, a length of an amino acid sequence sample is represented as L, a feature dimension is represented as D, an automatically augmented initial sequence feature sample is represented as x, and a reference sequence feature (that is, an augmented sequence feature sample) is represented as z, then x and z both are matrices with a size of L×D. The reconstruction error between the automatically augmented initial sequence feature sample and the reference sequence feature may be obtained by a root mean square reconstruction error calculation method, and the calculation formula is as follows:

$$\text{Error}(x, z) = \frac{1}{LD} \sum_{i=1}^{L} \sum_{j=1}^{D} (x_{ij} - z_{ij})^2$$

where $x_{ij}$ and $z_{ij}$ are elements in an $i^{th}$ row and a $j^{th}$ column in a matrix x and a matrix z respectively.

Figure 5:
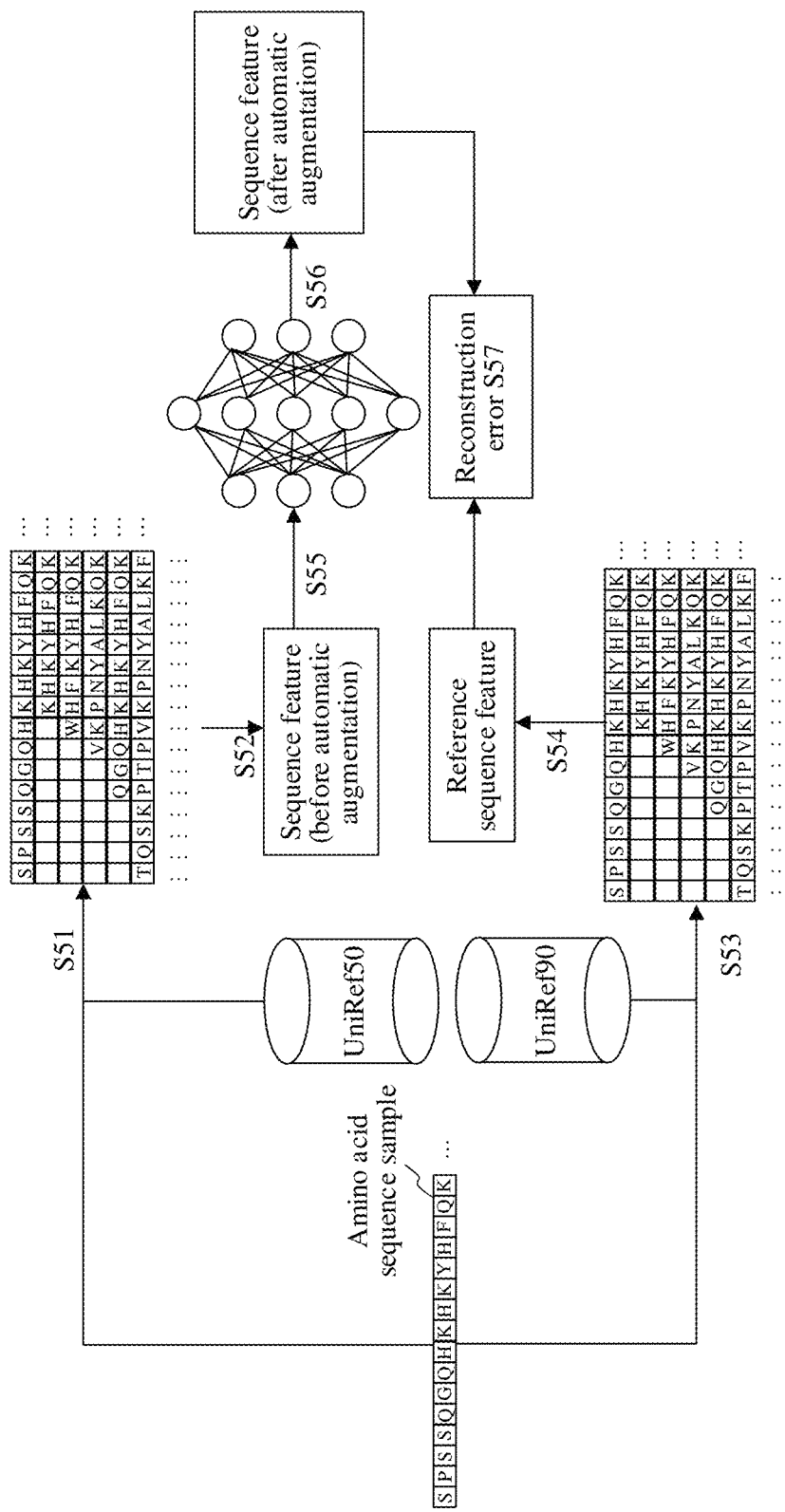
FIG. 5 is a schematic diagram of automatic sequence feature augmentation model training according to an embodiment shown in FIG. 4.

For example, the foregoing model training process may be shown in FIG. 5. FIG. 5 is a schematic diagram of sequence feature augmentation model training according to an embodiment of this disclosure. As shown in FIG. 5, the training process of the sequence feature augmentation model is as follows:

S51. A training device obtains an amino acid sequence sample, and performs a multi-sequence aligned data query operation on the amino acid sequence sample in a UniRef50 database, to obtain a multi-sequence aligned data result.

S52. The training device performs feature extraction on the multi-sequence aligned data result in S51 to obtain a sequence feature before automatic augmentation, which may also be referred to as an initial sequence feature sample.

S53. The training device performs the multi-sequence aligned data query operation on the foregoing amino acid sequence sample in a UniRef90 database, to obtain a multi-sequence aligned data result.

S54. The training device performs feature extraction on the multi-sequence aligned data result in S53 to obtain a reference sequence feature, which may also be referred to as an augmented sequence feature sample.

S55. The training device inputs the initial sequence feature sample into a sequence feature augmentation model.

S56. The sequence feature augmentation model outputs an augmented sequence feature, which may be referred to as an augmented initial sequence feature sample.

S57. The training device calculates a reconstruction error between the augmented sequence feature and the reference sequence feature as a loss function according to a formula, and trains and updates the sequence feature augmentation model according to the loss function.

In one implementation, when the sequence feature augmentation model is determined to be not converged according to the loss function value, the training device updates the model parameter in the sequence feature augmentation model according to the loss function value.

Before step 404 is performed, the training device may determine whether the model converges according to a loss function value. If the sequence feature augmentation model converges, the training device may end training and output the sequence feature augmentation model to a prediction device, and the prediction device predicts structure information of a protein.

Conversely, if the sequence feature augmentation model is determined not to converge, the training device may update the model parameter in the sequence feature augmentation model according to the loss function value.

In one implementation, when whether the model converges is determined, the training device compares the loss function value with a preset loss function threshold. If the loss function value is less than the loss function threshold, it means that a result outputted by the sequence feature augmentation model is close to a result obtained by query from the second database, indicating that the sequence feature augmentation model can achieve a good feature augmentation effect, and in this case, the model is determined to converge. Conversely, if the loss function value is not less than the loss function threshold, it means that a result outputted by the sequence feature augmentation model is far from a result obtained by query from the second database, indicating that the sequence feature augmentation model has not been able to achieve a good feature augmentation effect, and in this case, the model is determined to not converge.

In another implementation, when whether the model converges is determined, the training device compares the loss function value with a loss function value obtained in a previous round of the update process. If a difference between the loss function value obtained this time and the loss function value obtained in the previous round is less than a difference threshold, it means that the accuracy of the sequence feature augmentation model is improved slightly, and no significant improvement can be achieved by continuing training, and in this case, the model is determined to converge. Conversely, if the difference between the loss function value obtained this time and the loss function value obtained in the previous round is not less than the difference threshold, it means that the accuracy of the sequence feature augmentation model is improved greatly, and there may be a significant improvement by continuing training, and in this case, the model is determined to not converge.

In another implementation, when whether the model converges is determined, the training device compares the loss function value with a loss function value obtained in a previous round of the update process, and at the same time, compares the loss function value obtained this time with the loss function threshold. If the loss function value is less than the loss function threshold, and the difference between the loss function value obtained this time and the loss function value obtained in the previous round is less than the difference threshold, the model is determined to converge.

After the foregoing sequence feature augmentation model training is completed (that is, after the model is trained to convergence), the prediction device may predict structure information of a protein of which the structure is unknown according to the sequence feature augmentation model and the first database. The prediction process may refer to subsequent steps.

Step 405. A prediction device performs sequence alignment query in the first database according to an amino acid sequence of a protein to obtain multi-sequence aligned data.

The protein in this step may be a protein for which structure information prediction is required.

Step 406. The prediction device performs feature extraction on the multi-sequence aligned data to obtain an initial sequence feature.

Step 407. The prediction device processes the initial sequence feature by using a sequence feature augmentation model to obtain an augmented sequence feature of the protein.

For processes of the foregoing step 405 to step 407, refer to description in the embodiment shown in FIG. 3, and details are not described herein again.

Step 408. Predict structure information of the protein based on the augmented sequence feature.

In this embodiment of this disclosure, the prediction device may predict the augmented sequence feature by using a protein structure information prediction model to obtain the structure information of the protein. The protein structure information prediction model is a model trained according to a sequence feature of a protein sample and structure information of the protein sample.

In one implementation, the protein structure information prediction model is an existing machine learning model trained by other computer devices.

In this embodiment of this disclosure, the protein structure information prediction model used for predicting the structure information of the protein may alternatively be a model obtained through machine learning.

For example, the training device may obtain several protein samples with known structure information and an amino acid sequence of each protein sample; next, the training device performs sequence alignment query in a third database according to the amino acid sequence of the protein sample to obtain multi-sequence aligned data, and performs feature extraction on the multi-sequence aligned data obtained through the query to obtain an sequence feature of the protein sample; and then the protein structure information prediction model is trained by using the sequence feature of the protein sample as an input and using the structure information of the protein sample as labeled information. After the training is completed, the protein structure information prediction model may be applied to this step. The prediction device predicts the structure information of the protein by using the protein structure information prediction model according to the augmented sequence feature of the protein to be predicted.

In this embodiment of this disclosure, to improve the accuracy of predicting the structure information of the protein by using the protein structure information prediction model according to the augmented sequence feature of the protein to be predicted, the second database may be used as a database (that is, the third database) used in the training process of the protein structure information prediction model, that is, the second database and the third database may be the same database.

In one implementation, the second database and the third database may be different databases. For example, the third database may be a database with a larger data scale than the second database, and a data distribution similarity between the second database and the third database is higher than a similarity threshold. For example, the second database may be the UniRef90 database, and the third database may be the UniRef100 database.

Figure 6:
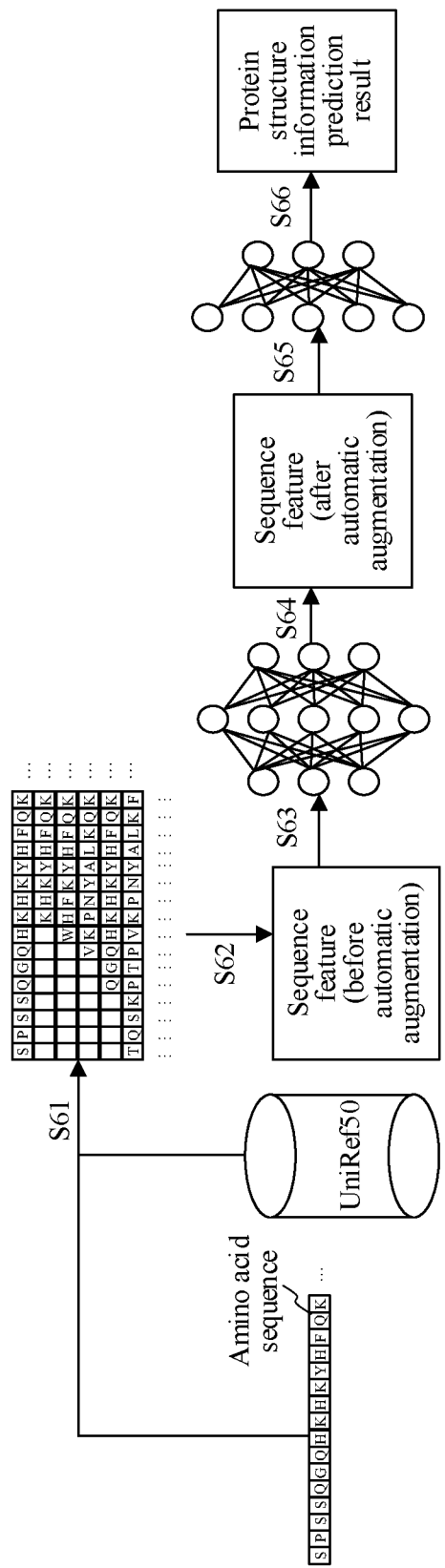
FIG. 6 is a schematic diagram of protein structure information prediction according to an embodiment shown in FIG. 4.

FIG. 6 is a schematic diagram of protein structure information prediction according to an embodiment of this disclosure. As shown in FIG. 6, the process of the protein structure information prediction is as follows:

S61. A prediction device obtains an amino acid sequence, and performs a multi-sequence aligned data query operation on the amino acid sequence in a UniRef50 database, to obtain a multi-sequence aligned data result.

S62. The prediction device performs feature extraction on the multi-sequence aligned data result to obtain a sequence feature before automatic augmentation.

S63. The prediction device inputs the sequence feature before automatic augmentation into a trained sequence feature augmentation model.

S64. The sequence feature augmentation model outputs an automatically augmented sequence feature.

S65. The prediction device inputs the automatically augmented sequence feature into a protein structure information prediction model.

S66. The protein structure information prediction model outputs a protein structure information prediction result corresponding to the amino acid sequence.

In the solution shown in this embodiment, the foregoing training device and prediction device may be the same computer device, that is, the computer device first trains the sequence feature augmentation model, and then predicts the structure information of the protein according to the sequence feature augmentation model.

Alternatively, the foregoing training device and prediction device may be different computer devices, that is, the training device first trains the sequence feature augmentation model and provides the sequence feature augmentation model to the prediction device, and the prediction device predicts the structure information of the protein according to the sequence feature augmentation model.

In summary, in the solution shown in the embodiments, by performing sequence alignment query on an amino acid sequence of a protein and performing feature extraction on multi-sequence aligned data, an augmented sequence feature of the protein is obtained by using a sequence feature augmentation model, and then structure information of the protein is predicted. By using the sequence feature augmentation model, the sequence alignment query only needs to be performed in a first database with a smaller data scale to obtain higher prediction accuracy. In addition, it takes less time to perform the sequence alignment query in the first database with a smaller data scale. Therefore, the foregoing solution can improve the prediction efficiency of protein structure information while ensuring the prediction accuracy of the protein structure information.

Figure 7:
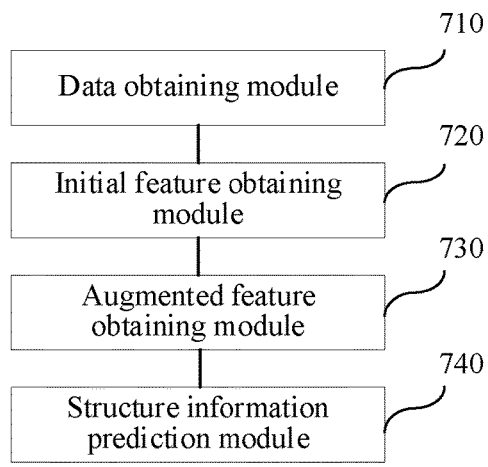
FIG. 7 is a structural block diagram of a protein structure information prediction apparatus according to an exemplary embodiment.

FIG. 7 is a structural block diagram of a protein structure information prediction apparatus according to an exemplary embodiment. The protein structure information prediction apparatus may be implemented as a part or all of a computer device in a form of hardware or a combination of software and hardware, to perform all or some steps in the method shown in the embodiment corresponding to FIG. 3 or FIG. 4. In this disclosure, the term module (and other similar terms such as unit, submodule, etc.) in this disclosure may refer to a software module, a hardware module, or a combination thereof. A software module (e.g., computer program) may be developed using a computer programming language. A hardware module may be implemented using processing circuitry and/or memory. Each module can be implemented using one or more processors (or processors and memory). Likewise, a processor (or processors and memory) can be used to implement one or more modules. Moreover, each module can be part of an overall module that includes the functionalities of the module. The protein structure information prediction apparatus may include:

a data obtaining module 710, configured to perform sequence alignment query in a first database according to an amino acid sequence of a protein to obtain multi-sequence aligned data;

an initial feature obtaining module 720, configured to perform feature extraction on the multi-sequence aligned data to obtain an initial sequence feature;

an augmented feature obtaining module 730, configured to process the initial sequence feature by using a sequence feature augmentation model to obtain an augmented sequence feature of the protein, the sequence feature augmentation model being a machine learning model trained by using an initial sequence feature sample and an augmented sequence feature sample, the initial sequence feature sample being obtained by performing sequence alignment query in the first database according to an amino acid sequence sample, the augmented sequence feature sample being obtained by performing sequence alignment query in a second database according to the amino acid sequence sample, and a data scale of the second database being greater than a data scale of the first database; and a structure information prediction module 740, configured to predict structure information of the protein based on the augmented sequence feature.

In one implementation, a data distribution similarity between the first database and the second database is higher than a similarity threshold.

In one implementation, the first database is a database obtained by randomly removing a specified proportion of data based on the second database. In another implementation, the removal of records in a database may follow a predetermined pattern or rule, and the pattern or rule maybe further be based on an index, or a keyword of the records. For another example, the removal of the records may be conducted in a random manner.

In one implementation, the sequence feature augmentation model is a fully convolutional network (FCN) model for one-dimensional sequence data, or a recurrent neural network (RNN) model including a plurality of layers of long short-term memory (LSTM) units or an RNN model including bidirectional LSTM units.

In one implementation, the initial sequence feature and the augmented sequence feature are position-specific scoring matrices (PSSMs).

In one implementation, the apparatus further includes:

an augmented sample obtaining module, configured to process the initial sequence feature sample by using the sequence feature augmentation model to obtain an augmented initial sequence feature sample; and a model update module, configured to update the sequence feature augmentation model according to the augmented initial sequence feature sample and the augmented sequence feature sample.

In one implementation, the model update module includes:

a loss function obtaining submodule, configured to perform a loss function calculation according to the augmented initial sequence feature sample and the augmented sequence feature sample to obtain a loss function value; and a parameter update submodule, configured to update a model parameter in the sequence feature augmentation model according to the loss function value.

In one implementation, the loss function obtaining submodule includes:

an error calculation unit, configured to calculate a reconstruction error between the augmented initial sequence feature sample and the augmented sequence feature sample; and a loss function acquisition unit, configured to acquire the reconstruction error as the loss function value.

In one implementation, the error calculation unit calculates a root mean square reconstruction error between the augmented initial sequence feature sample and the augmented sequence feature sample.

In one implementation, the model update module is configured to, when that the sequence feature augmentation model is determined to be not converged according to the loss function value, update the model parameter in the sequence feature augmentation model according to the loss function value.

In one implementation, the structure information prediction module 740 includes:

a structure information obtaining submodule, configured to predict the augmented sequence feature by using a protein structure information prediction model to obtain the structure information of the protein, where the protein structure information prediction model is a model trained according to a sequence feature of a protein sample and structure information of the protein sample.

In summary, in the solution shown in the embodiments of this disclosure, by performing sequence alignment query on an amino acid sequence of a protein and performing feature extraction on multi-sequence aligned data, an augmented sequence feature of the protein is obtained by using a sequence feature augmentation model, and then structure information of the protein is predicted. By using the sequence feature augmentation model, the sequence alignment query only needs to be performed in a first database with a smaller data scale to obtain higher prediction accuracy. In addition, it takes less time to perform the sequence alignment query in the first database with a smaller data scale. Therefore, the foregoing solution can improve the prediction efficiency of protein structure information while ensuring the prediction accuracy of the protein structure information.

Figure 8:
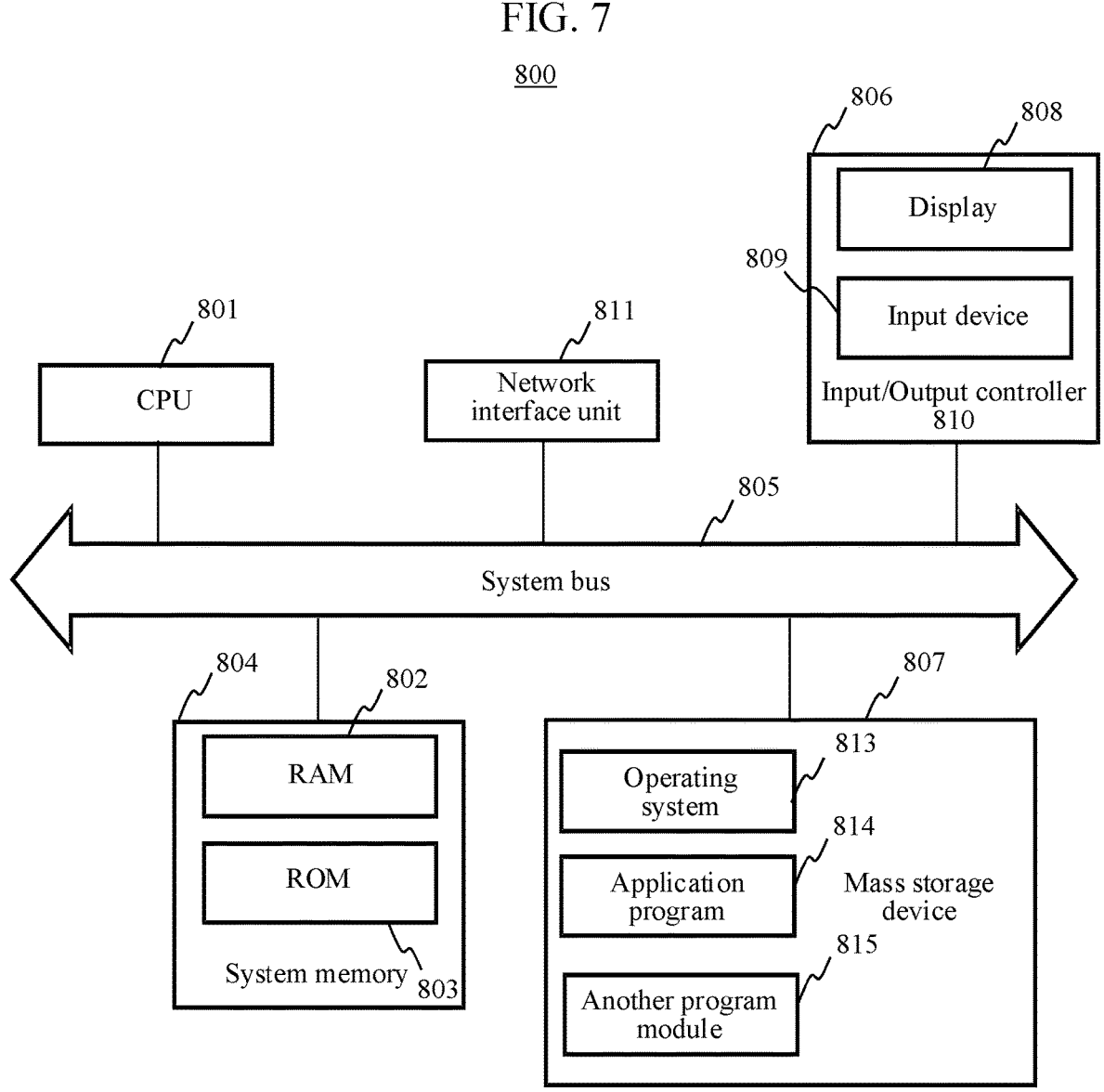
FIG. 8 is a schematic structural diagram of a computer device according to an exemplary embodiment.

FIG. 8 is a schematic structural diagram of a computer device according to an exemplary embodiment. The computer device may be implemented as the training device or the prediction device in the foregoing embodiments, or may be implemented as a combination of the training device and the prediction device. The computer device 800 includes a central processing unit (CPU) 801, a system memory 804 including a random access memory (RAM) 802 and a read-only memory (ROM) 803, and a system bus 805 connecting the system memory 804 and the CPU 801. The computer device 800 further includes a basic input/output system (I/O system) 806 helping transmit information between components in a computer, and a mass storage device 807 used for storing an operating system 813, an application program 814, and another program module 815.

The basic I/O system 806 includes a display 808 used for displaying information, and an input device 809, such as a mouse and a keyboard, used for a user to input information. The display 808 and the input device 809 are both connected to the CPU 801 by an input and output controller 810 connected to the system bus 805. The basic I/O system 806 may further include the input and output controller 810, to receive and process inputs from a plurality of other devices, such as a keyboard, a mouse, or an electronic stylus. Similarly, the input and output controller 810 further provides an output to a display screen, a printer, or another type of output device.

The mass storage device 807 is connected to the CPU 801 by a mass storage controller (not shown) connected to the system bus 805. The mass storage device 807 and an associated computer-readable medium provide non-volatile storage for the computer device 800. That is, the mass storage device 807 may include a computer-readable medium (not shown), such as a hard disk or a CD-ROM drive.

Without loss of generality, the computer-readable medium may include a non-transitory computer storage medium and a communication medium. The non-transitory computer storage medium includes volatile and non-volatile media, and removable and non-removable media implemented by using any method or technology used for storing information such as computer-readable instructions, data structures, program modules, or other data. The non-transitory computer storage medium includes a RAM, a ROM, an EPROM, an EEPROM, a flash memory, or another solid-state storage technology, a CD-ROM, a DVD, or another optical storage, a magnetic cassette, a magnetic tape, a magnetic disk storage, or another magnetic storage device. Certainly, a person skilled in the art may learn that the non-transitory computer storage medium is not limited to the foregoing several types. The system memory 804 and the mass storage device 807 may be collectively referred to as a memory.

The computer device 800 may be connected to the Internet or another network device by a network interface unit 811 connected to the system bus 805.

The memory further includes one or more programs. The one or more programs are stored in a memory. The CPU 801 implements the steps performed by the computer device in the protein structure information prediction method shown in FIG. 3 or FIG. 4 by executing the one or more programs.

This application further provides a computer program product, the computer program product, when run on a computer, causing the computer to perform the method according to the foregoing method embodiments.

Figure 9:
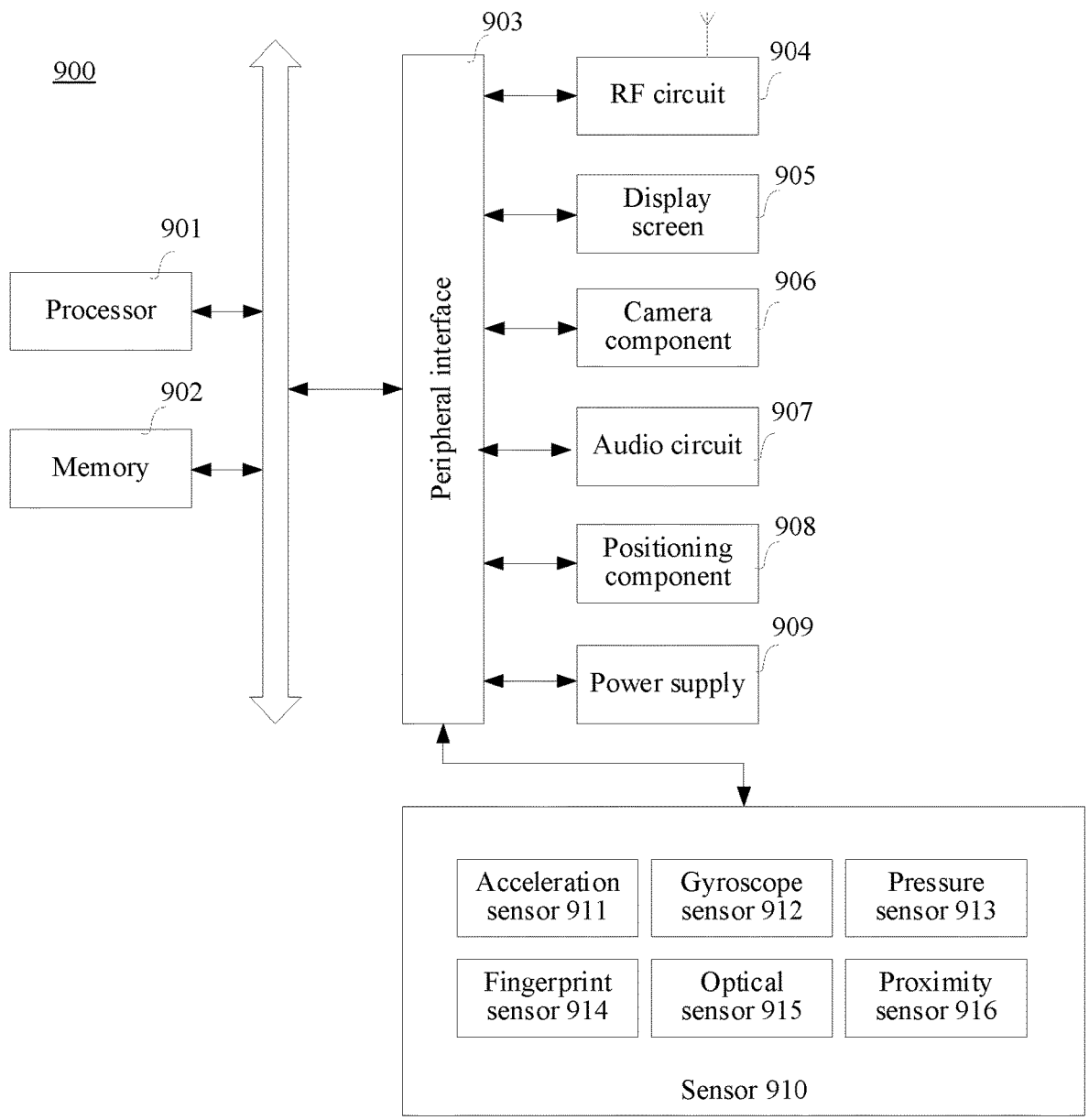
FIG. 9 is a schematic structural diagram of a terminal according to an exemplary embodiment.

FIG. 9 is a schematic structural diagram of a terminal 900 according to an exemplary embodiment of this disclosure. The terminal 900 may be a smartphone, a tablet computer, a Moving Picture Experts Group Audio Layer III (MP3) player, a Moving Picture Experts Group Audio Layer IV (MP4) player, a notebook computer, or a desktop computer. The terminal 900 may also be referred to as a user equipment, a portable terminal, a laptop terminal, a desktop terminal, or the like. The terminal may be implemented as the prediction device in the foregoing method embodiments. For example, the terminal may be implemented as the prediction device 120 in FIG. 1.

Generally, the terminal 900 includes a processor 901 and a memory 902.

The processor 901 may include one or more processing cores, for example, a 4-core processor or an 8-core processor. The processor 901 may be implemented in at least one hardware form of a digital signal processor (DSP), a field-programmable gate array (FPGA), and a programmable logic array (PLA). The processor 901 may alternatively include a main processor and a coprocessor. The main processor is configured to process data in an active state, also referred to as a CPU. The coprocessor is a low-power processor configured to process data in a standby state. In some embodiments, the processor 901 may be integrated with a graphics processing unit (GPU). The GPU is configured to be responsible for rendering and drawing content that a display needs to display. In some embodiments, the processor 901 may further include an AI processor. The AI processor is configured to process a computing operation related to machine learning.

The memory 902 may include one or more non-transitory computer-readable storage media. The non-transitory computer-readable storage media may be non-transient. The memory 902 may further include a high-speed RAM and a non-volatile memory, such as one or more magnetic disk storage devices or a flash storage device. In some embodiments, the non-transitory computer-readable storage medium in the memory 902 is configured to store at least one instruction, and the at least one instruction is used to be executed by the processor 901 to implement the protein structure information prediction method provided in the method embodiments of this disclosure.

In some embodiments, the terminal 900 may optionally include: a peripheral interface 903 and at least one peripheral. The processor 901, the memory 902, and the peripheral interface 903 may be connected by a bus or a signal cable. Each peripheral may be connected to the peripheral interface 903 by a bus, a signal cable, or a circuit board. Specifically, the peripheral includes: at least one of a radio frequency (RF) circuit 904, a touch display screen 905, a camera 906, an audio circuit 907, a positioning component 908, and a power supply 909.

The peripheral interface 903 may be configured to connect at least one peripheral related to I/O to the processor 901 and the memory 902. In some embodiments, the processor 901, the memory 902, and the peripheral interface 903 are integrated on the same chip or circuit board. In some other embodiments, any one or two of the processor 901, the memory 902, and the peripheral interface 903 may be implemented on an independent chip or circuit board. This is not limited in this embodiment.

The RF circuit 904 is configured to receive and transmit an RF signal, which is also referred to as an electromagnetic signal. The RF circuit 904 communicates with a communication network and other communication devices through the electromagnetic signal. The RF circuit 904 converts an electrical signal into an electromagnetic signal for transmission, or converts a received electromagnetic signal into an electrical signal. Optionally, the RF circuit 904 includes an antenna system, an RF transceiver, one or more amplifiers, a tuner, an oscillator, a digital signal processor, a codec chip set, a subscriber identity module card, and the like. The RF circuit 904 may communicate with another terminal by using at least one wireless communication protocol. The wireless communication protocol includes, but is not limited to, a world wide web, a metropolitan area network, an intranet, generations of mobile communication networks (2G, 3G, 4G, and 5G), a wireless local area network and/or a wireless fidelity (Wi-Fi) network. In some embodiments, the RF circuit 904 may further include a near field communication (NFC)-related circuit. This is not limited in this application.

The display screen 905 is configured to display a user interface (UI). The UI may include a graph, a text, an icon, a video, and any combination thereof. When the display screen 905 is a touch display screen, the display screen 905 is further capable of collecting a touch signal on or above a surface of the display screen 905. The touch signal may be inputted, as a control signal, to the processor 901 for processing. In this case, the display screen 905 may be further configured to provide a virtual button and/or a virtual keyboard that are/is also referred to as a soft button and/or a soft keyboard. In some embodiments, there may be one display screen 905 disposed on a front panel of the terminal 900. In some other embodiments, there may be at least two display screens 905 respectively disposed on different surfaces of the terminal 900 or designed in a foldable shape. In still some other embodiments, the display screen 905 may be a flexible display screen, disposed on a curved surface or a folded surface of the terminal 900. Even, the display screen 905 may be further set to have a non-rectangular irregular pattern, that is, a special-shaped screen. The display screen 905 may be made of materials such as a liquid crystal display (LCD), an organic light-emitting diode (OLED), or the like.

The camera component 906 is configured to capture images or videos. Optionally, the camera component 906 includes a front-facing camera and a rear-facing camera. Generally, the front-facing camera is disposed on a front panel of the terminal, and the rear-facing camera is disposed on a rear surface of the terminal. In some embodiments, there are at least two rear-facing cameras, which are respectively any of a main camera, a depth-of-field camera, a wide-angle camera, and a telephoto camera, to achieve background blur through fusion of the main camera and the depth-of-field camera, panoramic photographing and virtual reality (VR) photographing through fusion of the main camera and the wide-angle camera, or other fusion photographing functions. In some embodiments, the camera component 906 may further include a flash. The flash may be a single-color-temperature flash, or may be a double-color-temperature flash. The double-color-temperature flash refers to a combination of a warm-light flash and a cold-light flash, and may be used for light compensation under different color temperatures.

The audio circuit 907 may include a microphone and a speaker. The microphone is configured to collect sound waves of users and surroundings, and convert the sound waves into electrical signals and input the signals to the processor 901 for processing, or input the signals to the RF circuit 904 to implement voice communication. For the purpose of stereo collection or noise reduction, there may be a plurality of microphones, respectively disposed at different portions of the terminal 900. The microphone may be further an array microphone or an omni-directional collection type microphone. The speaker is configured to convert electrical signals from the processor 901 or the RF circuit 904 into sound waves. The speaker may be a conventional thin-film speaker or a piezoelectric ceramic speaker. When the speaker is the piezoelectric ceramic speaker, the speaker can not only convert electrical signals into sound waves audible to a human being, but also convert electrical signals into sound waves inaudible to the human being for ranging and other purposes. In some embodiments, the audio circuit 907 may also include an earphone jack.

The positioning component 908 is configured to determine a current geographic location of the terminal 900, to implement navigation or a location based service (LBS). The positioning component 908 may be a positioning component based on the Global Positioning System (GPS) of the United States, the BeiDou system of China, or the GALILEO System of the European Union.

The power supply 909 is configured to supply power to components in the terminal 900. The power supply 909 may be an alternating current, a direct current, a primary battery, or a rechargeable battery. When the power supply 909 includes the rechargeable battery, the rechargeable battery may be a wired charging battery or a wireless charging battery. The wired charging battery is a battery charged through a wired circuit, and the wireless charging battery is a battery charged through a wireless coil. The rechargeable battery may be further configured to support a fast charge technology.

In some embodiments, the terminal 900 further includes one or more sensors 910. The one or more sensors 910 include, but are not limited to, an acceleration sensor 911, a gyroscope sensor 912, a pressure sensor 913, a fingerprint sensor 914, an optical sensor 915, and a proximity sensor 916.

The acceleration sensor 911 may detect acceleration on three coordinate axes of a coordinate system established by the terminal 900. For example, the acceleration sensor 911 may be configured to detect components of gravity acceleration on the three coordinate axes. The processor 901 may control, according to a gravity acceleration signal collected by the acceleration sensor 911, the touch display screen 905 to display the UI in a landscape view or a portrait view. The acceleration sensor 911 may be further configured to collect motion data of a game or a user.

The gyroscope sensor 912 may detect a body direction and a rotation angle of the terminal 900, and may work with the acceleration sensor 911 to collect a 3D action performed by the user on the terminal 900. The processor 901 may implement the following functions according to data collected by the gyroscope sensor 912: motion sensing (for example, the UI is changed according to a tilt operation of the user), image stabilization during shooting, game control, and inertial navigation.

The pressure sensor 913 may be disposed on a side frame of the terminal 900 and/or a lower layer of the touch display screen 905. When the pressure sensor 913 is disposed on the side frame of the terminal 900, a holding signal of the user on the terminal 900 may be detected. The processor 901 performs left and right hand recognition or a quick operation according to the holding signal collected by the pressure sensor 913. When the pressure sensor 913 is disposed on the lower layer of the touch display screen 905, the processor 901 controls, according to a pressure operation of the user on the touch display screen 905, an operable control on the UI. The operable control includes at least one of a button control, a scroll-bar control, an icon control, and a menu control.

The fingerprint sensor 914 is configured to collect a fingerprint of the user, and the processor 901 recognizes an identity of the user according to the fingerprint collected by the fingerprint sensor 914, or the fingerprint sensor 914 recognizes the identity of the user according to the collected fingerprint. When the identity of the user is recognized as credible, the processor 901 authorizes the user to perform a related sensitive operation. The sensitive operation includes unlocking a screen, viewing encrypted information, downloading software, paying, changing a setting, and the like.

The fingerprint sensor 914 may be disposed on a front surface, a back surface, or a side surface of the terminal 900. When a physical button or a vendor logo is disposed on the terminal 900, the fingerprint sensor 914 may be integrated with the physical button or the vendor logo.

The optical sensor 915 is configured to acquire ambient light intensity. In an embodiment, the processor 901 may control display luminance of the touch display screen 905 according to the ambient light intensity collected by the optical sensor 915. Specifically, when the ambient light intensity is relatively high, the display luminance of the touch display screen 905 is increased; and when the ambient light intensity is relatively low, the display luminance of the touch display screen 905 is reduced. In another embodiment, the processor 901 may further dynamically adjust a camera parameter of the camera component 906 according to the ambient light intensity collected by the optical sensor 915.

The proximity sensor 916, also referred to as a distance sensor, is generally disposed on the front panel of the terminal 900. The proximity sensor 916 is configured to collect a distance between the user and the front face of the terminal 900. In an embodiment, when the proximity sensor 916 detects that the distance between the user and the front surface of the terminal 900 gradually becomes smaller, the touch display screen 905 is controlled by the processor 901 to switch from a screen-on state to a screen-off state; and when the proximity sensor 916 detects that the distance between the user and the front surface of the terminal 900 gradually becomes larger, the touch display screen 905 is controlled by the processor 901 to switch from the screen-off state to the screen-on state.

A person skilled in the art may understand that a structure shown in FIG. 9 constitutes no limitation on the terminal 900, and the terminal may include more or fewer components than those shown in the figure, or combine some components, or use a different component deployment.

A person of ordinary skill in the art may understand that all or some of the steps of the methods in the foregoing embodiments may be implemented by a program instructing relevant hardware. The program may be stored in a non-transitory computer-readable storage medium. The non-transitory computer-readable storage medium may be the computer-readable storage medium included in the memory in the foregoing embodiments, or may be a computer-readable storage medium that exists independently and that is not assembled in a terminal. The non-transitory computer-readable storage medium stores at least one instruction, at least one program, a code set, or an instruction set, and the at least one instruction, the at least one program, the code set, or the instruction set is loaded and executed by the processor to implement the protein structure information prediction method according to FIG. 3 or FIG. 4.

Optionally, the non-transitory computer-readable storage medium may include: a ROM, a RAM, a solid state drive (SSD), an optical disc, or the like. The RAM may include a resistance random access memory (ReRAM) and a dynamic random access memory (DRAM). The sequence numbers of the foregoing embodiments of this disclosure are merely for description purpose, and are not intended to indicate priorities of the embodiments.

According to an aspect of this application, a computer program product or a computer program is provided, including computer instructions, the computer instructions being stored in a non-transitory computer-readable storage medium. A processor of a computer device reads a computer instruction from a non-transitory computer-readable storage medium, and executes the computer instruction, so that the computer device performs the protein structure information prediction method provided in various optional implementations of the foregoing aspects.

A person of ordinary skill in the art may understand that all or some of the steps of the foregoing embodiments may be implemented by using hardware, or may be implemented by a program instructing relevant hardware. The program may be stored in a non-transitory computer-readable storage medium. The non-transitory storage medium may be a ROM, a magnetic disk, an optical disc, or the like.

The foregoing descriptions are merely exemplary embodiments of this disclosure, but are not intended to limit this application. Any modification, equivalent replacement, improvement, and the like made within the spirit and principle of this application shall fall within the protection scope of this application.

What is claimed is:

1. A method for predicting structure information of a protein, performed by a computer device, the method comprising:
performing sequence alignment query in a first database according to an amino acid sequence of the protein to obtain multi-sequence aligned data;
performing feature extraction on the multi-sequence aligned data to obtain an initial sequence feature;
processing the initial sequence feature by using a sequence feature augmentation model to obtain an augmented sequence feature of the protein, the sequence feature augmentation model being a machine learning model trained by using a sample initial sequence feature and a sample augmented sequence feature and updated according to an augmented sample initial sequence feature and the sample augmented sequence feature, the sample initial sequence feature being obtained by performing sequence alignment query in the first database according to a sample amino acid sequence, the sample augmented sequence feature being obtained by performing sequence alignment query in a second database according to the sample amino acid sequence, wherein a data scale of the second database being greater than a data scale of the first database, and the augmented sample initial sequence feature being obtained by processing the sample initial sequence feature by using the sequence feature augmentation model, wherein the sequence feature augmentation model comprises one of:
a fully convolutional network (FCN) model for one-dimensional sequence data;
a recurrent neural network (RNN) model comprising a plurality of layers of long short-term memory (LSTM) units; or
an RNN model comprising bidirectional LSTM units; and
predicting structure information of the protein based on the augmented sequence feature.

2. The method according to claim 1, wherein a data distribution similarity between the first database and the second database is higher than a similarity threshold.

3. The method according to claim 2, wherein the first database is obtained by removing a specified proportion of data based on the second database.

4. The method according to claim 1, wherein the initial sequence feature and the augmented sequence feature are position-specific scoring matrices (PSSMs).

5. The method according to claim 1, wherein updating the sequence feature augmentation model according to the augmented sample initial sequence feature and the sample augmented sequence feature comprises:
performing a loss function calculation according to the augmented sample initial sequence feature and the sample augmented sequence feature to obtain a loss function value; and
updating a model parameter in the sequence feature augmentation model according to the loss function value.

6. The method according to claim 5, wherein performing the loss function calculation according to the augmented sample initial sequence feature and the sample augmented sequence feature to obtain the loss function value comprises:
calculating a reconstruction error between the augmented sample initial sequence feature and the sample augmented sequence feature; and
acquiring the reconstruction error as the loss function value.

7. The method according to claim 6, wherein:
the reconstruction error comprises a root mean square reconstruction error; and
calculating the reconstruction error between the augmented sample initial sequence feature and the sample augmented sequence feature comprises:
calculating the root mean square reconstruction error between the augmented sample initial sequence feature and the sample augmented sequence feature.

8. The method according to claim 5, wherein updating the model parameter in the sequence feature augmentation model according to the loss function value comprises:
in determination that the sequence feature augmentation model is not converged according to the loss function value, updating the model parameter in the sequence feature augmentation model according to the loss function value.

9. The method according to claim 1, wherein before predicting structure information of the protein based on the augmented sequence feature, the method further comprises:
predicting based on the augmented sequence feature by using a protein structure information prediction model to obtain the structure information of the protein,
wherein the protein structure information prediction model is a model trained according to a sequence feature of a protein sample and structure information of the protein sample.

10. A device for predicting structure information of a protein, comprising a memory for storing computer instructions and a processor in communication with the memory, wherein, when the processor executes the computer instructions, the processor is configured to cause the device to:
perform sequence alignment query in a first database according to an amino acid sequence of the protein to obtain multi-sequence aligned data;
perform feature extraction on the multi-sequence aligned data to obtain an initial sequence feature;
process the initial sequence feature by using a sequence feature augmentation model to obtain an augmented sequence feature of the protein, the sequence feature augmentation model being a machine learning model trained by using a sample initial sequence feature and a sample augmented sequence feature and updated according to an augmented sample initial sequence feature and the sample augmented sequence feature, the sample initial sequence feature being obtained by performing sequence alignment query in the first database according to a sample amino acid sequence, the sample augmented sequence feature being obtained by performing sequence alignment query in a second database according to the sample amino acid sequence, wherein a data scale of the second database being greater than a data scale of the first database, and the augmented sample initial sequence feature being obtained by processing the sample initial sequence feature by using the sequence feature augmentation model, wherein the sequence feature augmentation model comprises one of:
  a fully convolutional network (FCN) model for one-dimensional sequence data;
  a recurrent neural network (RNN) model comprising a plurality of layers of long short-term memory (LSTM) units; or
  an RNN model comprising bidirectional LSTM units; and
predict structure information of the protein based on the augmented sequence feature.

11. The device according to claim 10, wherein a data distribution similarity between the first database and the second database is higher than a similarity threshold.

12. The device according to claim 11, wherein the first database is obtained by removing a specified proportion of data based on the second database.

13. The device according to claim 10, wherein the initial sequence feature and the augmented sequence feature are position-specific scoring matrices (PSSMs).

14. The device according to claim 10, wherein, when the processor is configured to cause the device to update the sequence feature augmentation model according to the augmented sample initial sequence feature and the sample augmented sequence feature, the processor is configured to cause the device to:
  perform a loss function calculation according to the augmented sample initial sequence feature and the sample augmented sequence feature to obtain a loss function value; and
  update a model parameter in the sequence feature augmentation model according to the loss function value.

15. The device according to claim 14, wherein, when the processor is configured to cause the device to perform the loss function calculation according to the augmented sample initial sequence feature and the sample augmented sequence feature to obtain the loss function value, the processor is configured to cause the device to:
  calculate a reconstruction error between the augmented sample initial sequence feature and the sample augmented sequence feature; and
  acquire the reconstruction error as the loss function value.

16. A non-transitory computer-readable storage medium for storing computer readable instructions, the computer readable instructions, when executed by a processor in a device, causing the processor to:
  perform sequence alignment query in a first database according to an amino acid sequence of a protein to obtain multi-sequence aligned data;
  perform feature extraction on the multi-sequence aligned data to obtain an initial sequence feature;
  process the initial sequence feature by using a sequence feature augmentation model to obtain an augmented sequence feature of the protein, the sequence feature augmentation model being a machine learning model trained by using a sample initial sequence feature and a sample augmented sequence feature and updated according to an augmented sample initial sequence feature and the sample augmented sequence feature, the sample initial sequence feature being obtained by performing sequence alignment query in the first database according to a sample amino acid sequence, the sample augmented sequence feature being obtained by performing sequence alignment query in a second database according to the sample amino acid sequence, wherein a data scale of the second database being greater than a data scale of the first database, and the augmented sample initial sequence feature being obtained by processing the sample initial sequence feature by using the sequence feature augmentation model, wherein the sequence feature augmentation model comprises one of:
    a fully convolutional network (FCN) model for one-dimensional sequence data;
    a recurrent neural network (RNN) model comprising a plurality of layers of long short-term memory (LSTM) units; or
    an RNN model comprising bidirectional LSTM units; and
  predict structure information of the protein based on the augmented sequence feature.

* * * * *